United States Patent
Kessler et al.

(10) Patent No.: US 7,983,754 B2
(45) Date of Patent: Jul. 19, 2011

(54) LEAD INSERTION VISIBILITY

(75) Inventors: Amy K. Kessler, Minnetonka, MN (US); Wayne M. Hector, Shoreview, MN (US); David G Schaenzer, Minneapolis, MN (US); Thomas Majewski, Lino Lakes, MN (US); David W. Scott, Forest Lake, MN (US); Mike R. Klardie, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 808 days.

(21) Appl. No.: 11/216,623

(22) Filed: Aug. 31, 2005

(65) Prior Publication Data

US 2007/0049985 A1    Mar. 1, 2007

(51) Int. Cl.
*A61N 1/375* (2006.01)

(52) U.S. Cl. ........................................................ 607/37

(58) Field of Classification Search .............. 607/37, 607/38
See application file for complete search history.

(56) References Cited

U.S. PATENT DOCUMENTS

| | | | |
|---|---|---|---|
| 3,908,668 A | 9/1975 | Bolduc | |
| 4,012,103 A * | 3/1977 | Lunquist | 439/181 |
| 4,072,154 A | 2/1978 | Anderson et al. | |
| 4,142,532 A * | 3/1979 | Ware | 607/37 |
| 4,226,244 A | 10/1980 | Coury et al. | |
| 5,683,433 A | 11/1997 | Carson | |
| 5,716,390 A * | 2/1998 | Li | 607/127 |
| 5,766,042 A | 6/1998 | Ries et al. | |
| 6,112,121 A | 8/2000 | Paul et al. | |
| 6,192,276 B1 | 2/2001 | Strandberg | |
| 6,672,895 B2 | 1/2004 | Scheiner | |
| 6,817,905 B2 | 11/2004 | Zart et al. | |
| 2003/0100220 A1 | 5/2003 | Scheiner | |
| 2004/0122481 A1* | 6/2004 | Tidemand et al. | 607/37 |
| 2005/0131481 A1 | 6/2005 | Ries et al. | |

FOREIGN PATENT DOCUMENTS

| | | |
|---|---|---|
| DE | 10247672 A1 | 4/2004 |
| WO | WO9842408 A | 10/1998 |
| WO | WO0013746 A | 3/2000 |
| WO | WO03092808 A | 11/2003 |
| WO | WO2006047043 A | 5/2006 |

* cited by examiner

*Primary Examiner* — Carl H. Layno
*Assistant Examiner* — Jon-Eric C. Morales
(74) *Attorney, Agent, or Firm* — Carol F. Barry

(57) ABSTRACT

An implantable medical device system that includes a housing containing an electrical circuit and a connector header mounted on the housing. A first inner surface of the connector header forms a connector bore adapted for receiving a lead connector assembly for electrically coupling a medical lead to the circuitry contained in the housing, and one of the connector header and the lead connector includes a visibly modified surface for facilitating visual verification of full insertion of the medical lead connector assembly in the connector bore.

30 Claims, 4 Drawing Sheets

LEAD INSERTION VISIBILITY

TECHNICAL FIELD

The invention relates to medical devices, and, more particularly, to configurations of implantable medical device connector headers and corresponding lead connectors for facilitating verification of proper lead insertion into a connector bore.

BACKGROUND

In the medical field, a wide variety of implantable devices are used in conjunction with a medical lead for delivering a therapy or monitoring a physiological condition at a targeted site within the body. The lead carries sensors or electrodes for deployment to the targeted therapy delivery or monitoring site. For example, implantable leads are commonly used to form part of implantable cardiac pacemaker systems that provide therapeutic stimulation to the heart by sensing electrical activity of the heart and delivering pacing, cardioversion, or defibrillation pulses via electrodes disposed on the leads, typically near the distal ends of the leads.

Electrodes or sensors are coupled to conductors extending to the proximal lead end where each conductor is coupled to a connector included in a lead connector assembly. An implantable device is generally provided with a connector header having bores adapted for receiving a corresponding lead connector assembly. The connector bores have electrical contacts which mate with the connectors included on the lead connector assembly. When the lead connector assembly is properly inserted in the connector bore, any electrodes or sensors carried by the lead are electrically coupled to the circuitry contained in the implantable medical device via feedthroughs which connect the connector header contacts to the device circuitry. Thus, proper insertion of the lead connector assembly into the connector bore is essential for effective therapy delivery or monitoring function of the implantable medical device system.

New configurations of implantable device systems, for example down-sized leads and devices and connector headers having multiple connector bores, can make visual verification of proper lead insertion a challenge. Improper insertion can result in faulty connection between the lead and the implanted device. If not recognized at the time of the initial implant procedure, an improperly inserted lead problem requires the patient to undergo a second surgical procedure in order to troubleshoot and correct the problem. Such procedures pose added risk and inconvenience to the patient and should be avoided.

BRIEF DESCRIPTION OF THE DRAWINGS

Aspects and features of the present invention will be readily appreciated as the same becomes better understood by reference to the following detailed description when considered in connection with the accompanying drawings, wherein.

DETAILED DESCRIPTION

In the following detailed description, references are made to illustrative embodiments of methods and apparatus for carrying out the invention. It is understood that other embodiments can be utilized without departing from the scope of the invention. The invention is directed toward a connection system for coupling one or more medical leads to an implantable medical device (IMD), such as a pacemaker, cardioverter/defibrillator, muscle stimulator, neurostimulator, drug pump, physiological monitor, or any other type of implantable medical device known in the art. In particular, the various embodiments of the invention are directed toward connection systems that facilitate visual verification of proper insertion of a lead connector assembly within a bore of a connector header. The connector header is generally attached to a hermetically sealed housing of the IMD and includes elements for electrically coupling the IMD to the lead connector assembly and may include elements for retaining the lead connector assembly within the connector bore.

Figure 1:
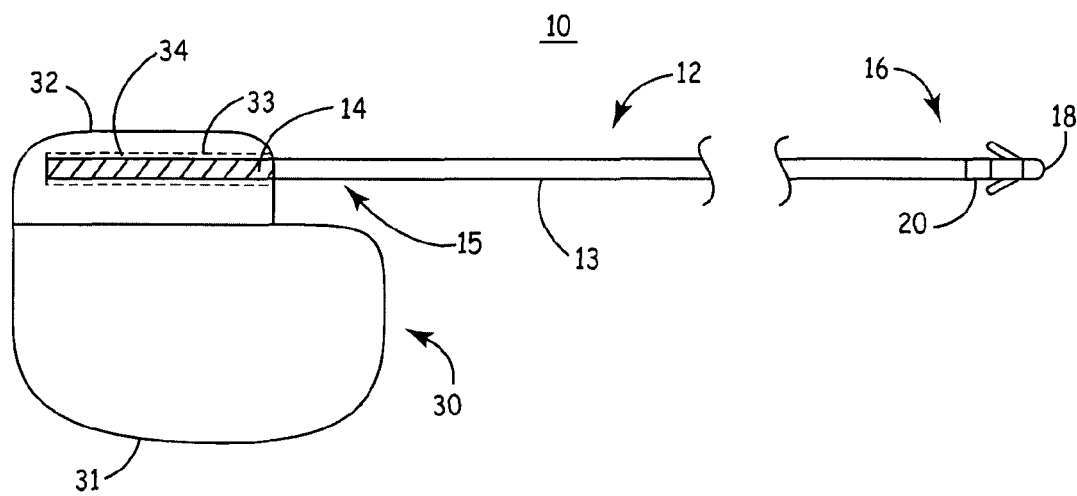
FIG. 1 is a schematic diagram of a medical device according to an embodiment of the present invention.

For example, an IMD system 10 is illustrated in FIG. 1 which includes an IMD 30 and an associated medical lead 12. Known circuitry and other components (not shown) of IMD 30 are enclosed in hermetically sealed housing 31. Connector header 32 is attached to housing 31. Connector header 32 is provided with at least one connector bore 34 formed by inner surface 33. Connector bore 34 is adapted for receiving a connector assembly 14 provided at the proximal end 15 of lead 12. Lead 12 is shown having an elongated body 13 carrying two electrodes, a tip electrode 18 and ring electrode 20 at or near the distal end 16 of lead 12. Lead connector assembly 14 is provided with connectors electrically coupled to the electrodes 18 and 20 via conductors extending from connector assembly 14 to distal lead end 16. In various embodiments, lead 12 may be provided with any number of electrodes or physiological sensors, each with corresponding connectors provided on connector assembly 14 to allow coupling to IMD 30.

Connector bore 34 includes contacts for establishing electrical connection with the connectors of connector assembly 14. The contacts included in connector bore 34 are coupled to the circuitry housed within housing 31 via feedthroughs according to methods known in the art.

Connector header 32 is typically formed from a rigid polymer such as polyurethane or epoxy. Connector header 32 is typically translucent and substantially colorless allowing observation of lead connector assembly 14 within connector bore 34. Glare and the particular contour of the connector header 32 can make visual verification of full insertion of lead connector assembly 14 within connector bore 34 difficult. Furthermore, the lead connector assembly 14 typically includes silver connector elements and polyurethane or silicone insulating sheaths that are substantially colorless or only slightly colored such that the visual contrast between the lead connector assembly 14 and the translucent connector header 32 is limited.

Figure 2:
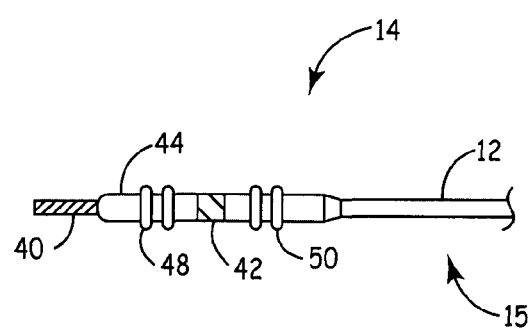
FIG. 2 is a plan view of an exemplary lead connector assembly of the device of FIG. 1.

As will be described in greater detail herein, various embodiments of the invention provide for a visibly modified surface of elements included in the connector header 32 and/or elements included in the lead connector assembly 14. The visibly modified surface enhances the visual contrast between the connector header 32 and the connector assembly 14, thereby facilitating visual verification of proper lead insertion. The terms "visibly modified surface" or "visually modified surface" as used herein refers generally to the result of any application or modification applied to an element as a whole, to any portion of the element, or to any surface of the element that affects the visual appearance of the element. For example, the affect on the visual appearance may be a visual change in color and/or a visual change in texture FIG. 2 is a plan view of a lead connector assembly 14. Lead connector assembly 14 is commonly known as an "in-line" connector assembly and includes a connector pin 40 and a connector ring 42. Connector pin 40 and connector ring 42 are arranged "in line", separated by an insulating sheath 44. Connector assembly 14 may be provided with one or more sealing rings 48 and 50 to resist the ingress of body fluids into the connector bore after implantation. Connector pin 40 is typically coupled to a tip electrode 18 (shown in FIG. 1) via a conductor extending the length of lead 12. Connector ring 42 is typically coupled to a ring electrode 20 (shown in FIG. 1) via a corresponding conductor. While connector assembly 14 is shown here having a single connector ring, multiple connector rings may be provided for various multi-polar or multiple sensor lead configurations. Multi-polar in-line connector assemblies are known in the art. While in-line connectors are commonly used in modern IMDs, embodiments of the invention may include other types of lead connector assemblies such as bi-furcated or tri-furcated connector assemblies.

Connector pin 40 and connector ring 42 are typically fabricated from a conductive metal such as titanium or stainless steel. As such, connector pin 40 and connector ring 42 generally have a shiny finish and are silver in color. When connector assembly 14 is inserted in connector bore 34 (FIG. 1), the silver-colored lead assembly connectors 40 and 42 may be difficult to observe within the translucent connector header 32. In one embodiment of the invention, connector pin 40 and/or connector ring 42 are surface modified to improve the visibility of connector pin 40 and/or connector ring 42 within connector bore 34.

For example, in one embodiment, connector pin 40 and/or connector ring 42 are modified by gold plating or gold sputtering. In another embodiment, connector pin 40 and/or connector ring 42 are surface-modified by titanium-nitride coating. The gold plating, gold sputtering, or TiN coating provides enhanced visibility of connector pin 40 and/or connector ring 42 within the translucent connector header 32. The surface modification of the connectors 40 and 42 may have additional benefits such as increased electrical conductivity.

In yet another embodiment, the insulating sheath 44 may be provided with a color for enhancing visual contrast between the lead connector assembly 14 and the connector header components for facilitating visual verification of lead assembly insertion within a connector bore. Additionally or alternatively, sealing rings 48 and/or 50 may be provided with a color for enhancing visual contrast between lead connector assembly 14 and the connector header.

Figure 3:
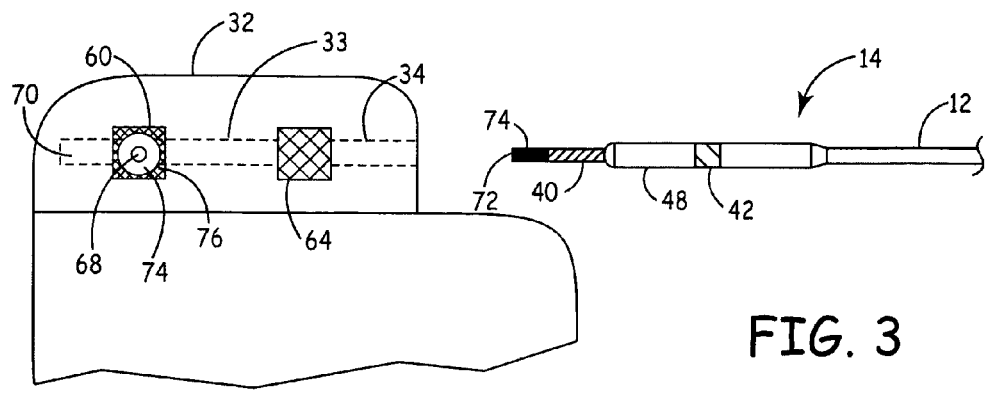
FIG. 3 is a schematic diagram of a medical device illustrating modifications made for facilitating visual verification of lead assembly insertion according to an embodiment of the present invention.

FIG. 3 is a plan view of connector header 32 illustrating modifications made for facilitating visual verification of lead assembly insertion according to an embodiment of the present invention. Connector header 32 is shown in FIG. 3 having a connector bore 34 adapted for receiving a bi-polar lead. Connector bore 34 is provided with electrical contacts 60 and 64 for electrically coupling with a connector pin 40 and a connector ring 42 of a corresponding lead connector assembly 14. Electrical contact 60 is typically a connector block for receiving and electrically coupling with connector pin 40. Electrical contact 64 is commonly a multi-beam connector for receiving and electrically coupling with connector ring 42. In other embodiments of the invention, any type of connector header contacts known in the art may be used.

Furthermore, in various embodiments of the invention, connector header 32 may include one or more bores for receiving a corresponding number of leads. Each bore may have any number of contacts for electrical coupling with corresponding lead assembly connectors. It is recognized that the invention may be practiced using a variety of connector bore and lead assembly configurations. When lead assembly 14 is fully inserted in connector bore 34, the proximal tip 72 of the connector pin 40 comes to rest in the tip cavity 70, extending beyond connector block contact 60. As such, the proximal tip 72 of connector pin 40 should be visible within connector bore 34 when lead assembly 14 is properly inserted.

In one embodiment, at least a portion 74 of connector pin 40 near proximal tip 72 is modified to enhance the visibility of proximal portion 74 within tip cavity 70, thereby facilitating visual verification of lead assembly insertion. Since the proximal portion 74 of connector pin 40 is not in contact with connector block 60, surface modification of proximal portion 74 for enhanced visibility may not retain the same electrical conductivity properties of the remainder of connector pin 40 that makes electrical contact with connector block 60.

In another embodiment of the invention, connector block contact 60 is modified to provide greater contrast between block contact 60 and connector pin 40. When both block contact 60 and connector pin 40 are silver in color, for example, visual verification of proximal tip 72 of connector pin 40 extending into pin cavity 70 may be hindered due to the lack of contrast between connector pin 40 and block contact 60. As such, block contact 60 may be modified by providing a visible surface of block contact 60 with a color that enhances the contrast between connector pin 40 and block contact 60. The block contact 60 and/or multi-beam contact 64 may be provided with a contrasting color to enhance visual verification of lead insertion using methods such as, but not limited to, anodizing, gold plating, gold sputtering, or titanium nitride coating. For example, connector block 60 and/or multi-beam contact 64 may be fabricated as a magenta anodized titanium contact. In another example, visible modification of connector block contact 60 and/or multi-beam contact 64 may include roughening the surface of the block contact 60 and multi-beam contact 64, for example using grit blasting methods to reduce glare and give a visually darker appearance to the contacts 60 and 64 thereby achieving enhanced visual contrast with elements of lead connector assembly 14.

Figure 4A:
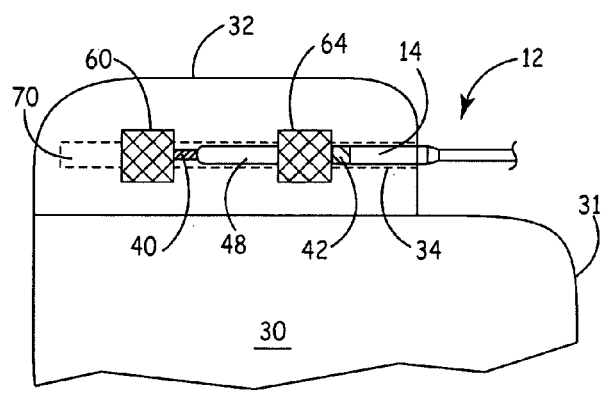
FIG. 4A is a side view of a connector header of a medical device having a lead connector assembly partially inserted in a connector bore according to an embodiment of the present invention.

FIG. 4A is a side view of connector header 32 with lead connector assembly 14 partially inserted in connector bore 34. Connector pin 40 and connector ring 42 are visible on the distal side of connector block contact 60 and multi-beam contact 64, respectfully, i.e. connector pin 40 is visible to the right of block contact 60 and connector ring 42 is visible to the right of multi-beam contact 64 in the orientation illustrated in FIG. 4A.

Figure 4B:
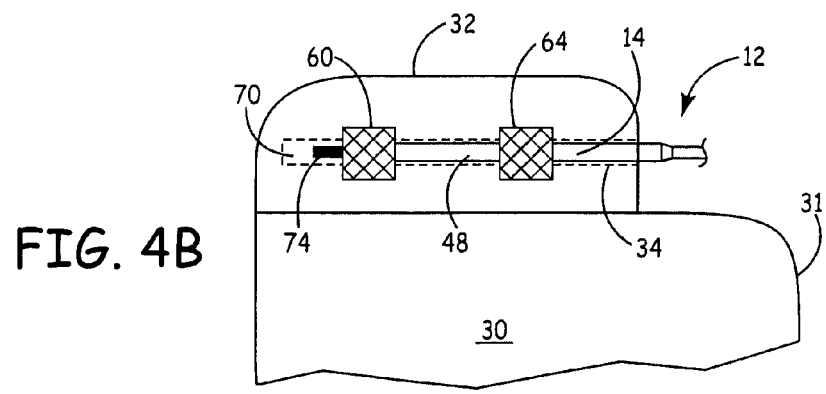
FIG. 4B is a side view of a connector header of a medical device having a lead connector assembly fully inserted in a connector bore according to an embodiment of the present invention.

FIG. 4B is a side view of connector header 32 with lead connector assembly 14 fully inserted in connector bore 34 according to an embodiment of the present invention. The proximal portion 74 of connector pin 40 is visible in tip cavity 70. Connector pin 40 is not be visible on the distal side of block contact 60. Connector ring 42 comes to rest within multi-beam contact 64 and is not visible. As such, enhanced visual contrast between the proximal end portion 74 of connector pin 40 and connector header 32 elements, such as block contact 60, will facilitate visual verification of proper lead insertion. Such enhanced contrast is achieved by visually modifying, through color or texture, one or more surfaces of the lead connector assembly elements, e.g., connector pin 40, connector ring 42, insulation sheath 48 or sealing rings 50 (shown in FIG. 2) and/or one or more surfaces of the connector header elements, e.g., connector bore 34, contact block 60, or multibeam contact 64.

Referring again to FIG. 3, connector header 32 may include a fastener or retaining member for stabilizing the position of lead connector assembly 14 within connector bore 34. In one fastener arrangement, the connector block contact 60 is provided with a threaded bore (not visible in FIG. 3) aligned with a grommet aperture 76 in which a penetrable grommet 74 is disposed. A setscrew 68 is threaded into the threaded bore of the connector block contact 60 and can be rotated to tighten the setscrew against the lead connector pin 40 after lead connector assembly 14 insertion into connector bore 34. The grommet 74 is typically formed from a resilient polymer material, such as silicone rubber. In accordance with one embodiment of the invention, grommet 74 is provided with a color to enhance visual contrast between grommet 74 and lead assembly elements. A fastener arrangement, such as a setscrew and grommet configuration, for stabilizing the lead assembly position within connector bore 34 may be provided according to arrangements known in the art. Elements included in a fastener arrangement may be provided as opaque or semi-opaque, colored, or roughened elements for enhancing visibility of a lead assembly received in a connector bore. Various example embodiments of connector header assemblies which may be used with the present invention are generally disclosed in U.S. Pat. No. 3,908,668 to Bolduc, U.S. Pat. No. 4,226,244 to Coury et al., U.S. Pat. No. 5,766, 042 to Ries et al., and U.S. Pat. No. 6,817,905 to Zart et al., all of which patents are hereby incorporated herein by reference in their entirety.

Figure 5:
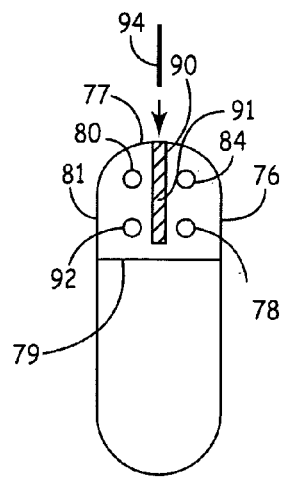
FIG. 5 is an end view of a connector header of a medical device according to an embodiment of the present invention.

FIG. 5 is an end view of a connector header according to an embodiment of the present invention. A contrast bore 90 is formed by inner surface 91. Contrast bore 90 is formed adjacent a connector bore to improve visual contrast between a lead connector assembly received within the connector bore and the connector header 76. In the example shown in FIG. 5, connector header 76 is shown having four connector bores 78, 80, 82, 84. A contrast bore 90 may be formed in connector header 76 adjacent to any selected connector bore 78, 80, 82, or 84. Contrast bore 90 is filled with a contrasting agent to enhance the visibility of a lead connector assembly received within the adjacent connector bore 78, 80, 82, or 84.

For example, contrast bore 90 may be back-filled with an opaque medium such as titanium dioxide medical adhesive. In other embodiments, a contrast member 94 is press fit into contrast bore 90. Contrast member 94 may be a pin, rod, peg, block or any other geometric member adapted for insertion into contrast bore 90. Contrast member 94 is formed from any implantable grade, opaque or semi-opaque polymeric or metal material. For example, contrast member 94 may be formed from anodized titanium or a colored plastic. Alternatively, contrast member 94 may be a coating, liquid adhesive, or any other contrast agent disposed within contrast bore 90 or applied to the inner surface 91 forming contrast bore 90 in order to enhance the visibility of a lead connector assembly received within the adjacent connector bore.

Contrast bore 90 can be formed by drilling or molding bore 90 in connector header 76. Connector bore 90 is shown having an opening on top surface 77 of connector header 76. Contrast bore 90 is formed substantially perpendicular to connector bores 80 and 82. A substantially perpendicular contrast bore 90 can alternatively be formed extending into connector header 76 from bottom surface 79. Contrast bore 90 entering from top connector header surface 77 may be formed with a depth such that bore 90 is adjacent upper connector bore 80 only. Contrast bore 90 may alternatively be formed with a depth such that bore 90 extends past both upper connector bore 80 and lower connector bore 82. When viewed through side surface 81 of connector header 32, visibility of a lead connector assembly received in connector bore 80 or 82 is improved against the contrasting background provided by contrast bore 90.

Figure 6:
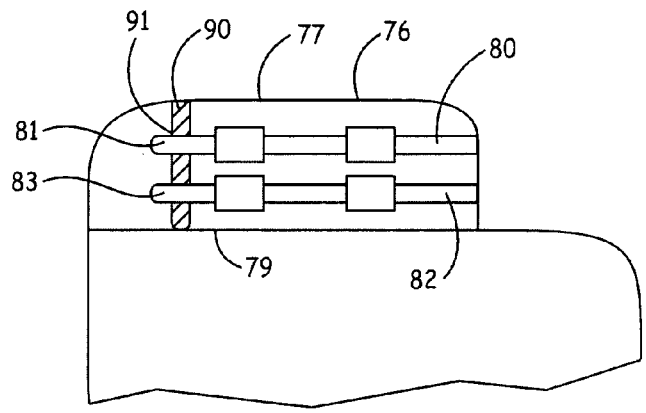
FIG. 6 is a side view of a connector header of a medical device having a contrast bore extending substantially perpendicular to one or more connector bores according to an embodiment of the present invention.

FIG. 6 is a side view of a connector header having a contrast bore extending substantially perpendicular to one or more connector bores. In the embodiment illustrated in FIG. 5, contrast bore 90 is formed adjacent tip cavity 81 and tip cavity 83 of respective connector bores 80 and 82 to enhance visibility of a lead connector pin received in tip cavity 81 or tip cavity 83. In various embodiments, contrast bore 90 can be formed adjacent any selected portion of connector bores 80 and 82 where visual contrast with received lead connector elements is desired for facilitating visual verification of lead insertion.

Figure 7:
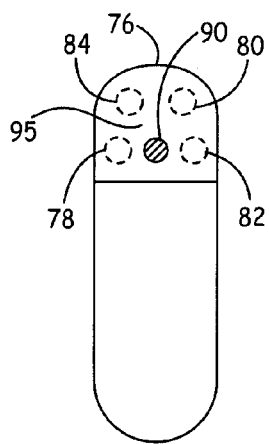
FIG. 7 is an end view of a connector header of a medical device having a contrast bore extending substantially parallel to a selected connector bore according to an embodiment of the present invention.

FIG. 7 is an end view of a connector header having a contrast bore extending substantially parallel to a selected connector bore according to an embodiment of the present invention. In FIG. 7, contrast bore 90 is formed by drilling or molding contrast bore 90 substantially parallel to connector bore 82 with an opening on a proximal surface 95 of connector header 76.

Figure 8:
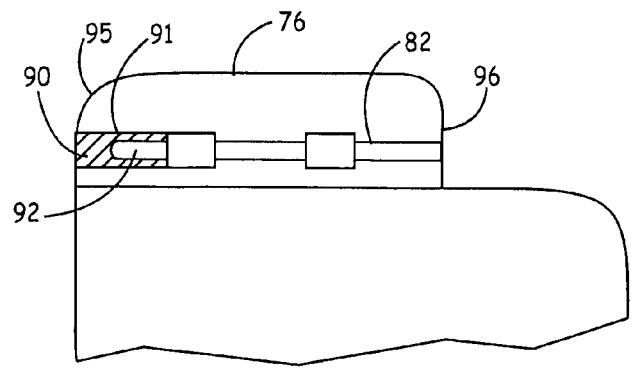
FIG. 8 is a side view of the connector header of FIG. 7.

FIG. 8 is a side view of the connector header shown in FIG. 7. Contrast bore 90 is formed in connector header 76 extending from proximal surface 95, substantially parallel to connector bore 82. Proximal surface 95 is the surface opposite the distal surface 96, where connector bore openings receive a lead assembly. Contrast bore 90 extends adjacent tip cavity 92 of connector bore 82 to enhance visibility of a lead connector pin received within tip cavity 92. Contrast bore 90 may extend approximately parallel along the entire length of connector bore 82 or any portion thereof.

Contrast bore 90 may be provided as a generally cylindrical or planar bore extending from any connector header surface, adjacent any selected connector bore or portion thereof. It is recognized that numerous geometries may be conceived for providing a contrast bore that creates a visually contrasting background to a connector bore or portion thereof for facilitating lead insertion verification.

Figure 9:
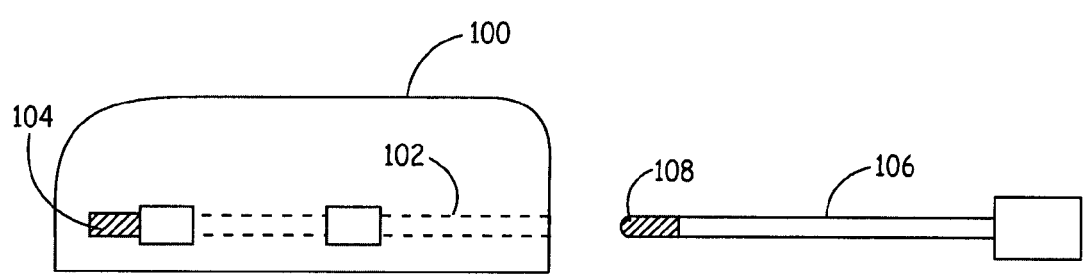
FIG. 9 is a side view of a connector header having a roughened connector bore surface according to an embodiment of the present invention.

FIG. 9 is a side view of a connector header 100 having a roughened connector bore surface according to an embodiment of the present invention. In some embodiments, the surface of connector bore 102 is modified to enhance visual contrast between lead connector assembly elements and connector header 100. Glare off the translucent surfaces of the connector header 100 may hinder visual verification of lead insertion. By roughening the surface of connector bore 102, glare can be reduced, improving the visibility of a lead connector assembly within connector bore 102. As such, one embodiment of the invention includes fabricating connector bore 102 with a roughened surface along at least a portion of connector bore 102. For example, the tip cavity 104 of connector bore 102 may be fabricated with a roughened surface.

During a molding process for manufacturing connector header 100, a generally cylindrical form 106, commonly referred to as a "core pin," is used to create connector bore 102. In one method for manufacturing connector header 100, core pin 106 is provided with a roughened surface 108 along at least a portion of its length, for example the portion that will correspond to tip cavity surface 104 of the final molded bore 102. Roughened surface 108 may be formed using electrical discharge machining, grit blasting or other techniques for roughing a surface.

When core pin 106 is removed from connector header 100, the tip cavity surface 104 of bore 102 that was against the roughened surface 108 of core pin 106 will be rough. The rough tip cavity surface 104 will reduce glare and thereby enhance visibility of a lead connector pin received within bore 102, facilitating visual verification of lead insertion.

Thus, a system for coupling medical leads to implantable medical devices has been presented in the foregoing description with reference to specific embodiments. It is appreciated that various modifications to the referenced embodiments may be made without departing from the scope of the invention as set forth in the following claims.

What is claimed is:

1. A medical device, comprising:
a housing;
an elongated lead having a connector assembly with a connector pin at a proximal end of the lead; and
a connector header mounted to the housing, wherein the connector header comprises translucent material defining a connector bore adapted for receiving the connector assembly, the connector header comprising an electrical contact positioned along the connector bore to provide an electrical coupling to the connector pin of the connector assembly when the connector assembly is received within the connector bore,
wherein at least a portion of the connector pin is visually modified to enhance visual contrast between the connector pin and the connector header.

2. The medical device of claim 1, wherein at least a portion of an inner surface of the connector bore is visually modified to enhance visual contrast between the visually modified inner surface and the connector pin.

3. The medical device of claim 2, wherein the visually modified portion of inner surface of the connector bore comprises a roughened surface.

4. The medical device of claim 2, wherein the connector bore comprises a tip cavity and wherein the visually modified portion of the inner surface includes the tip cavity.

5. The medical device of claim 1, wherein at least a portion of a surface of the electrical contact is visually modified to enhance visual contrast between the visually modified surface of the electrical contact and the connector pin.

6. The medical device of claim 5, wherein the visually modified surface of the electrical contact comprises a roughened surface.

7. The medical device of claim 5, wherein the visually modified surface of the electrical contact comprises an anodized titanium contact layer.

8. The medical device of claim 5, wherein the visually modified surface of the electrical contact comprises one of a gold plated surface, a gold sputtered surface, and a titanium-nitride coated surface.

9. The medical device of claim 1, further comprising a fastener to secure the connector assembly within the connector bore, wherein at least a portion of a surface of the fastener is visually modified to enhance visual contrast between the visually modified surface of the fastener and the connector pin.

10. The medical device of claim 9, wherein the fastener comprises a grommet and at least a portion of a surface of the grommet is visually modified.

11. The medical device of claim 1, wherein the connector header further comprises a contrast bore extending adjacent at least a portion of the connector bore, wherein a contrast member is disposed in the contrast bore, and wherein the contrast member provides a contrasting background for the connector pin when the connector header is viewed through the translucent material of the connector header.

12. The device of claim 11, wherein the connector bore extends along a first axis and the contrast bore extends along an second axis, and wherein the first axis is parallel to the second axis.

13. The device of claim 11, wherein the contrast member comprises semi-opaque material.

14. A medical device, comprising:
a housing;
an elongated lead having a connector assembly with a connector pin at a proximal end of the lead; and
a connector header mounted to the housing, wherein the connector header comprises translucent material defining a connector bore adapted for receiving the connector assembly, the connector header comprising an electrical contact positioned along the connector bore to provide an electrical coupling to the connector pin of the connector assembly when the connector assembly is received within the connector bore,
wherein at least a portion of an inner surface of the translucent material defining the connector bore is visually modified to enhance visual contrast between the visually modified inner surface and the connector pin.

15. The medical device of claim 14, wherein the visually modified portion of inner surface of the translucent material defining the connector bore comprises a roughened surface.

16. The medical device of claim 14, wherein the connector bore comprises a tip cavity and wherein the visually modified portion of the inner surface of the translucent material defining the connector bore includes the tip cavity.

17. The medical device of claim 15, wherein at least a portion of a surface of the electrical contact is visually modified to enhance visual contrast between the visually modified surface of the electrical contact and the connector pin.

18. The medical device of claim 17, wherein the visually modified surface of the electrical contact comprises a roughened surface.

19. The medical device of claim 17, wherein the visually modified surface of the electrical contact comprises an anodized titanium contact layer.

20. The medical device of claim 17, wherein the visually modified surface of the electrical contact comprises one of a gold plated surface, a gold sputtered surface, and a titanium-nitride coated surface.

21. The medical device of claim 14, further comprising a fastener to secure the connector assembly within the connector bore, wherein at least a portion of a surface of the fastener is visually modified to enhance visual contrast between the visually modified surface of the fastener and the connector pin.

22. The medical device of claim 21, wherein the fastener comprises a grommet and at least a portion of a surface of the grommet is visually modified.

23. The medical device of claim 14, wherein the connector header further comprises a contrast bore extending adjacent at least a portion of the connector bore, wherein a contrast member is disposed in the contrast bore, and wherein the contrast member provides a contrasting background for the connector pin when the connector header is viewed through the translucent material of the connector header.

24. A medical device for use with an elongated lead, the elongated lead having a connector assembly with a connector pin at a proximal end of the lead, the device comprising:
a housing; and
a connector header mounted to the housing, wherein the connector header comprises translucent material, wherein the connector header defines:
 a connector bore configured for receiving a connector assembly of an elongated lead,
 a side surface extending parallel to the connector bore, and
 a contrast bore extending adjacent at least a portion of the connector bore,
wherein the connector bore is located between the contrast bore and the side surface, wherein the connector header comprises:
 an electrical contact positioned along the connector bore to provide an electrical coupling to a connector pin of the connector assembly of the elongated lead when the connector assembly is received within the connector bore, and
 a contrast member disposed within the contrast bore, wherein the contrast member provides a contrasting background for the connector pin when the connector header is viewed through the translucent material of the side surface of the connector header.

25. The device of claim 24, wherein the contrast member comprises semi-opaque material.

26. A medical device for use with an elongated lead, the elongated lead having a connector assembly with a connector pin at a proximal end of the lead, the device comprising:
a housing; and
a connector header mounted to the housing, wherein the connector header comprises translucent material, wherein the connector header defines a connector bore configured for receiving a connecter assembly of an elongated lead, wherein the connector header comprises an electrical contact positioned along the connector bore to provide an electrical coupling to a connector pin of the connector assembly of the elongated lead when the connector assembly is received within the connector bore,
wherein at least a portion of a surface of the electrical contact is visually modified to enhance visual contrast between the visually modified surface of the electrical contact and the connector pin.

27. The medical, device of claim 26, wherein the visually modified outer surface of the electrical contact comprises a roughened surface.

28. The medical device of claim 26, wherein the visually modified outer surface of the electrical contact comprises an anodized titanium contact layer.

29. The medical device of claim 26, wherein the visually modified outer surface of the electrical contact comprises one of a gold plated surface, a gold sputtered surface, and a titanium-nitride coated surface.

30. A medical device for use with an elongated lead, the elongated lead having a connector assembly with a connector pin at a proximal end of the lead, the device comprising:
a housing; and
a connector header mounted to the housing, wherein the connector header comprises translucent material, wherein the connector header defines:
 a connector bore configured for receiving a connecter assembly of an elongated lead, and
 a contrast bore extending adjacent at least a portion of the connector bore,
wherein the connector bore extends along a first axis and the contrast bore extends along
an second axis, and wherein the first axis is parallel to the second axis, wherein the connector header comprises:
 an electrical contact positioned along the connector bore to provide an electrical coupling to a connector pin of the connector assembly of the elongated lead when the connector assembly is received within the connector bore, and
 a contrast member disposed within the contrast bore, wherein the contrast member provides a contrasting background for the connector pin when the connector header is viewed through the translucent material of the connector header.

* * * * *